United States Patent
Okamura

(10) Patent No.: US 7,787,590 B2
(45) Date of Paint: Aug. 31, 2010

(54) RADIOGRAPHIC APPARATUS AND RADIATION DETECTION SIGNAL PROCESSING METHOD

(75) Inventor: Shoichi Okamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 365 days.

(21) Appl. No.: 12/090,244

(22) PCT Filed: Nov. 14, 2005

(86) PCT No.: PCT/JP2005/020837

§ 371 (c)(1),
(2), (4) Date: Apr. 14, 2008

(87) PCT Pub. No.: WO2007/055024

PCT Pub. Date: May 18, 2007

(65) Prior Publication Data

US 2009/0257556 A1    Oct. 15, 2009

(51) Int. Cl.
G01N 23/04    (2006.01)
(52) U.S. Cl. ..................................... 378/62; 378/98.11
(58) Field of Classification Search ............... 378/4–20, 378/62, 98.8, 98.11, 98.12, 207; 250/370.08, 250/370.09
See application file for complete search history.

(56) References Cited

U.S. PATENT DOCUMENTS

2004/0156481 A1    8/2004    Okamura et al.

FOREIGN PATENT DOCUMENTS

| JP | 09-009153 A | 1/1997 |
|---|---|---|
| JP | 2000-121579 A | 4/2000 |
| JP | 2002-152593 A | 5/2002 |
| JP | 2002-152594 A | 5/2002 |
| JP | 2002-171444 A | 6/2002 |
| JP | 2003-130957 A | 5/2003 |
| JP | 2004-242741 A | 9/2004 |
| JP | 2004-261489 A | 9/2004 |

OTHER PUBLICATIONS

International Search Report for the Application No. PCT/JP2005/020837 dated Dec. 20, 2005.

*Primary Examiner*—Courtney Thomas
(74) *Attorney, Agent, or Firm*—Cheng Law Group, PLLC

(57) ABSTRACT

A radiographic apparatus according to this invention carries out lag correction by applying lag data based on a plurality of radiation detection signals acquired in time of non-irradiation before first irradiation, to both first and second radiation detection signals. Thus, lag correction is possible without acquiring lag components between the first irradiation and second irradiation. Also in the case of carrying out two radiation irradiations (first irradiation and second irradiation) for one image, lag-behind parts included in the radiation detection signals can be removed simply from the radiation detection signals.

7 Claims, 9 Drawing Sheets

RADIOGRAPHIC APPARATUS AND RADIATION DETECTION SIGNAL PROCESSING METHOD

TECHNICAL FIELD

This invention relates to a radiographic apparatus and a radiation detection signal processing method for obtaining radiographic images based on radiation detection signals resulting from radiation emitted to and transmitted through an object under examination. More particularly, the invention relates to a technique for eliminating lag-behind parts from the radiation detection signals.

BACKGROUND ART

An example of radiographic apparatus is an imaging apparatus that obtains X-ray images by detecting X rays. This apparatus used an image intensifier as an X-ray detecting device in the past. In recent years, a flat panel X-ray detector (hereinafter called simply "FPD") has come to be used instead.

The FPD has a sensitive film laminated on a substrate, detects radiation incident on the sensitive film, converts the detected radiation into electric charges, and stores the electric charges in capacitors arranged in a two-dimensional array. The electric charges are read by turning on switching elements, and are transmitted as radiation detection signals to an image processor. The image processor obtains an image having pixels based on the radiation detection signals.

The FPD is lightweight and free from complicated detecting distortions compared with the image intensifier used heretofore. Thus, the, FPD has advantages in terms of apparatus construction and image processing.

However, when the FPD is used, the X-ray detection signals include lag-behind parts. A lag-behind part results in an afterimage from X-ray irradiation in a preceding imaging event appearing as an artifact on a next X-ray image.

Particularly, in a fluoroscopy that performs X-ray irradiation continually at short time intervals (e.g. 1/30 second), time lags of the lag-behind parts have influences serious enough to hinder diagnosis.

Artifacts due to lag-behind parts are reduced by reducing long time constant components of the lag-behind parts by using backlight (see Patent Document 1, for example), or by regarding the lag-behind parts as a total of exponential functions having a plurality of time constants, and performing a lag correction by recursive computation using these exponential functions (see Patent Document 2, for example).

Where backlight is used as disclosed in the Patent Document 1 noted above, the construction becomes complicated by a construction required for backlight. Particularly where backlight is used in an FPD having a lightweight construction, the construction must become heavy and complicated again. In the case of Patent Document 2, the lag correction must be carried out by performing recursive computations the number of times X-ray detection signals are sampled. This renders the lag correction complicated and cumbersome.

In order to remove lag-behind parts included in X-ray detection signals simply from the X ray detection signals, it is conceivable in performing a lag correction, to acquire a plurality of X-ray detection signals in time of non-irradiation before irradiation of X rays in an imaging event, acquire a lag image based on the X-ray detection signals, and use this image to remove the lags from a product X-ray image.

On the other hand, apart from the above method of acquiring an X-ray image by lag correction, an energy subtraction (DES) method (hereinafter referred to simply as the "DES method" as appropriate) is known, which acquires a new image from two images, i.e. an X-ray image obtained by high energy X-ray irradiation and an image by low energy X-ray irradiation (see Patent Documents 3-6, for example). This method is used when obtaining chest images in which rib signals are suppressed, for example. As shown in FIG. 11, the DES method performs, for example, a first irradiation for 120 kV and 10 ms, and immediately thereafter performs a second irradiation for 60 kV and 50 to 100 ms. In practice, an idle time of about 200 ms occurs between the first irradiation and second irradiation due to the functional limitations of the apparatus. A subtraction process is carried out by appropriately weighting the images obtained by the first irradiation and second irradiation, respectively. The subtraction process is carried out using the following equation (1), for example:

$$I_{DES} = I_1 \times W_1 - I_2 \times W_2 \tag{1}$$

where, $I_{DES}$ is an energy subtraction image, $I_1$ is an X-ray detection signal (intensity) acquired from the first irradiation, $I_2$ is an X-ray detection signal (intensity) acquired from the second irradiation, $W_1$ is a weight of $I_1$, and $W_2$ is a weight of $I_2$. Instead of being limited to the above equation (1), subtraction may be carried out between respective logarithms as in Patent Documents 3-6 noted above.

[Patent Document 1]
Unexamined Patent Publication No. H9-9153 (pages 3-8, FIG. 1)
[Patent Document 2]
Unexamined Patent Publication No. 2004-242741 (pages 4-11, FIGS. 1 and 3-6)
[Patent Document 3]
Unexamined Patent Publication No. 2002-171444
[Patent Document 4]
Unexamined Patent Publication No. 2002-152594
[Patent Document 5]
Unexamined Patent Publication No. 2002-152593
[Patent Document 6]
Unexamined Patent Publication No. 2000-121579

DISCLOSURE OF THE INVENTION

Problems to be Solved by the Invention

However, when the above DES method is applied to lag correction, there arises the following problem. In the DES method also, lag components of a lag-behind part are included in every X-ray detection signal. In this case, as shown in FIG. 12, the image based on the X-ray detection signal of the first irradiation has a superimposition of lag components (see $K_0$ in FIG. 12) resulting from the preceding irradiation. The image based on the X-ray detection signal of the second irradiation has an additional superimposition of lag components (see $K_1$ in FIG. 12) resulting from the first irradiation besides that of the above lag components (see $K_0$ in FIG. 12). It is necessary to perform an interimage computation process such as of subtraction after acquiring the images by the two irradiations. It is therefore necessary to minimize time between the first irradiation and second irradiation, to avoid a shift between the two images due to motions of the object under examination. Thus, there is no time allowed for acquiring lag components ($K_0$ and $K_1$ in FIG. 12) (lag collection) between the first irradiation and second irradiation. When the DES method is applied to lag correction, there arises a problem that a lag collection for the image in the second irradiation cannot be carried out between the first irradiation and second irradiation.

This invention has been made having regard to the state of the art noted above, and its object is to provide a radiographic apparatus and a radiation detection signal processing method for eliminating lag-behind parts from radiation detection signals in a simple way also when radiation is emitted twice for one image.

Means for Solving the Problem

To fulfill the above object, this invention employs the following construction.

A radiographic apparatus according to this invention is a radiographic apparatus for obtaining radiographic images based on radiation detection signals, comprising a radiation emitting device for emitting radiation toward an object under examination; a radiation detecting device for detecting radiation transmitted through the object; (1) a non-irradiation signal acquiring device for acquiring a plurality of radiation detection signals detected from the radiation detecting device in time of non-irradiation before irradiation of the radiation in an imaging event; (2) an irradiation signal acquiring device for acquiring the radiation detection signals detected from the radiation detecting device in time of irradiation of the radiation in the imaging event; (3) a lag correcting device operable, when irradiation is carried out twice across a non-irradiation, the earlier irradiation being regarded as a first irradiation and the later irradiation being regarded as a second irradiation, radiation detection signals acquired by said irradiation signal acquiring device during said first irradiation being regarded as first radiation detection signals, and radiation detection signals acquired by said irradiation signal acquiring device during said second irradiation being regarded as second radiation detection signals, for applying lag data based on a plurality of radiation detection signals acquired by the non-irradiation signal acquiring device in time of non-irradiation before the first irradiation to both said first radiation detection signals and said second radiation detection signals, to remove lag-behind parts included in the radiation detection signals from the radiation detection signals, thereby performing a lag correction of the lag-behind parts; and (4) a radiographic image acquiring device for acquiring radiographic images by performing subtraction using the first radiation detection signals and the second radiation detection signals for which the lag correction has been carried out by the lag correcting device.

According to the radiographic apparatus of this invention, the non-irradiation signal acquiring device acquires a plurality of radiation detection signals detected from the radiation detecting device in time of non-irradiation before the radiation irradiation in an imaging event, and the irradiation signal acquiring device acquires radiation detection signals detected from the radiation detection device in time of radiation irradiation in the imaging event. When irradiation is carried out twice across a non-irradiation, the earlier irradiation is regarded as a first irradiation and the later irradiation is regarded as a second irradiation, radiation detection signals acquired by the irradiation signal acquiring device during the first irradiation are regarded as first radiation detection signals, and radiation detection signals acquired by the irradiation signal acquiring device during the second irradiation are regarded as second radiation detection signals. Then, the lag correcting device applies lag data based on a plurality of radiation detection signals acquired by the non-irradiation signal acquiring device in time of non-irradiation before the first irradiation to both the first radiation detection signals and the second radiation detection signals, to remove lag-behind parts included in the radiation detection signals from the radiation detection signals, thereby performing a lag correction of the lag-behind parts. The radiographic image acquiring device acquires radiographic images by performing subtraction using the first radiation detection signals and the second radiation detection signals for which the lag correction has been carried out by the lag correcting device. Thus, there is no need to carry out lag correction by performing recursive computations corresponding in number to the number of times of sampling to acquire radiation detection signals as performed in Patent Document 2 noted hereinbefore. Further, since lag correction is carried out by applying lag data based on the plurality of radiation detection signals acquired by the non-irradiation signal acquiring device in time of non-irradiation before the first irradiation, to both the first and second radiation detection signals, respectively, lag correction is possible without acquiring lag components between the first irradiation and second irradiation. Therefore, also in the case of carrying out two radiation irradiations (first irradiation and second irradiation) for one image, lag-behind parts included in the radiation detection signals can be removed simply from the radiation detection signals.

It is also not necessary to use backlight as in Patent Document 1 noted hereinbefore, and thus the construction of the apparatus is not complicated.

A radiation detection signal processing method according to this invention is a radiation detection signal processing method for performing a signal processing to obtain radiographic images based on radiation detection signals detected by irradiating an object under examination, said signal processing comprising (a) a non-irradiation signal acquiring step for acquiring a plurality of radiation detection signals in time of non-irradiation before irradiation of the radiation in an imaging event; (b) a first irradiation signal acquiring step for acquiring radiation detection signals in time of first irradiation which is a radiation irradiation time in the imaging event after said non-irradiation signal acquiring step; (c) a second irradiation signal acquiring step for acquiring radiation detection signals in time of second irradiation which is a radiation irradiation time in the imaging event following non-irradiation after said first irradiation signal acquiring step; (d) a lag correcting step for applying lag data based on the radiation detection signals acquired in said non-irradiation signal acquiring step to both first radiation detection signals which are the radiation detection signals acquired in said first irradiation signal acquiring step, and second radiation detection signals which are the radiation detection signals acquired in said second irradiation signal acquiring step, to remove lag-behind parts included in the radiation detection signals from the radiation detection signals, thereby performing a lag correction of the lag-behind parts; and (e) a radiographic image acquiring step for acquiring radiographic images by performing subtraction using the first radiation detection signals and the second radiation detection signals for which the lag correction has been carried out in the lag correcting step.

According to the radiation detection signal processing method of this invention, the non-irradiation signal acquiring step acquires a plurality of radiation detection signals detected from the radiation detecting device in time of non-irradiation before the radiation irradiation in an imaging event, and the first irradiation signal acquiring step acquires radiation detection signals in time of first irradiation which is a radiation irradiation time in the imaging event after the non-irradiation signal acquiring step. Further, the second irradiation signal acquiring step acquires radiation detection signals in time of second irradiation which is a radiation irradiation time in the imaging event following non-irradiation after the above first irradiation signal acquiring step. In the lag correcting step, lag data based on the radiation detection signals acquired in the non-irradiation signal acquiring step is applied to both first radiation detection signals which are the radiation detection signals acquired in the first irradiation signal acquiring step, and second radiation detection signals which are the radiation detection signals acquired in the second irradiation signal acquiring step, to remove lag-behind parts included in the radiation detection signals from the radiation detection signals, thereby performing a lag correction of the lag-behind parts. The radiographic image acquiring step acquires radiographic images by performing subtraction using the first radiation detection signals and the second radiation detection signals for which the lag correction has been carried out in the lag correcting step. Thus, there is no need to carry out lag correction by performing recursive computations corresponding in number to the number of times of sampling to acquire radiation detection signals as performed in Patent Document 2 noted hereinbefore. Further, since lag correction is carried out by applying lag data based on the plurality of radiation detection signals acquired in the non-irradiation signal acquiring step before the first irradiation, to both the first and second radiation detection signals, respectively, lag correction is possible without acquiring lag components between the first irradiation and second irradiation. Therefore, also in the case of carrying out two radiation irradiations (first irradiation and second irradiation) for one image, lag-behind parts included in the radiation detection signals can be removed simply from the radiation detection signals.

The second radiation detection signals acquired in the second irradiation signal acquiring step may be regarded as including lag components due to the first radiation detection signals acquired in the first irradiation signal acquiring step. Then, in the radiation detection signal processing method of this invention, preferably, a further lag correction is carried out for the second radiation detection signals to remove lags from the second radiation detection signals using values based on the first radiation detection signals. Also where such a further lag correction is carried out for the second radiation detection signals, lag correction is possible by using the values based on the first radiation detection signals, without acquiring lag components between the first irradiation and second irradiation.

In one example, the values based on the first radiation detection signals and used in the lag correction for the second radiation detection signals are expressed by a function of the first radiation detection signals. In another example, such values are matched beforehand with the first radiation detection signals, respectively.

The former, function, and also the latter, the values matched beforehand with the first radiation detection signals, respectively, is/are determined from information on radiation detection acquired before a series of radiation detection signals, acquiring conditions before the series of radiation detection signals, or peculiar information on a radiation detecting device that detects radiation detection.

EFFECTS OF THE INVENTION

With the radiographic apparatus and radiation detection signal processing method according to this invention, lag correction is carried out by applying lag data based on a plurality of radiation detection signals acquired in time of non-irradiation before first irradiation, to both first and second radiation detection signals. Thus, lag correction is possible without acquiring lag components between the first irradiation and second irradiation. Therefore, also in the case of carrying out two radiation irradiations (first irradiation and second irradiation) for one image, lag-behind parts included in the radiation detection signals can be removed simply from the radiation detection signals.

DESCRIPTION OF REFERENCES

2 . . . X-ray tube
3 . . . flat panel X-ray detector (FPD)
9a . . . non-irradiation signal acquiring unit
9b . . . irradiation signal acquiring unit
9c . . . lag correcting unit
9d X-ray image acquiring unit
I . . . X-ray detection signals
A . . . first correction data
B . . . second correction data
M . . . patient

BEST MODE FOR CARRYING OUT THE INVENTION

In a radiation detection signal processing method, lag correction is carried out by applying, along with first and second radiation detection signals, lag data based on a plurality of radiation detection signals acquired in time of non-irradiation preceding a first irradiation. Lag correction is thereby made possible without acquiring lag components between the first irradiation and a second irradiation. This fulfills the object of eliminating lag-behind parts from radiation detection signals in a simple way also when radiation is emitted twice for one image.

EMBODIMENT 1

Figure 1:
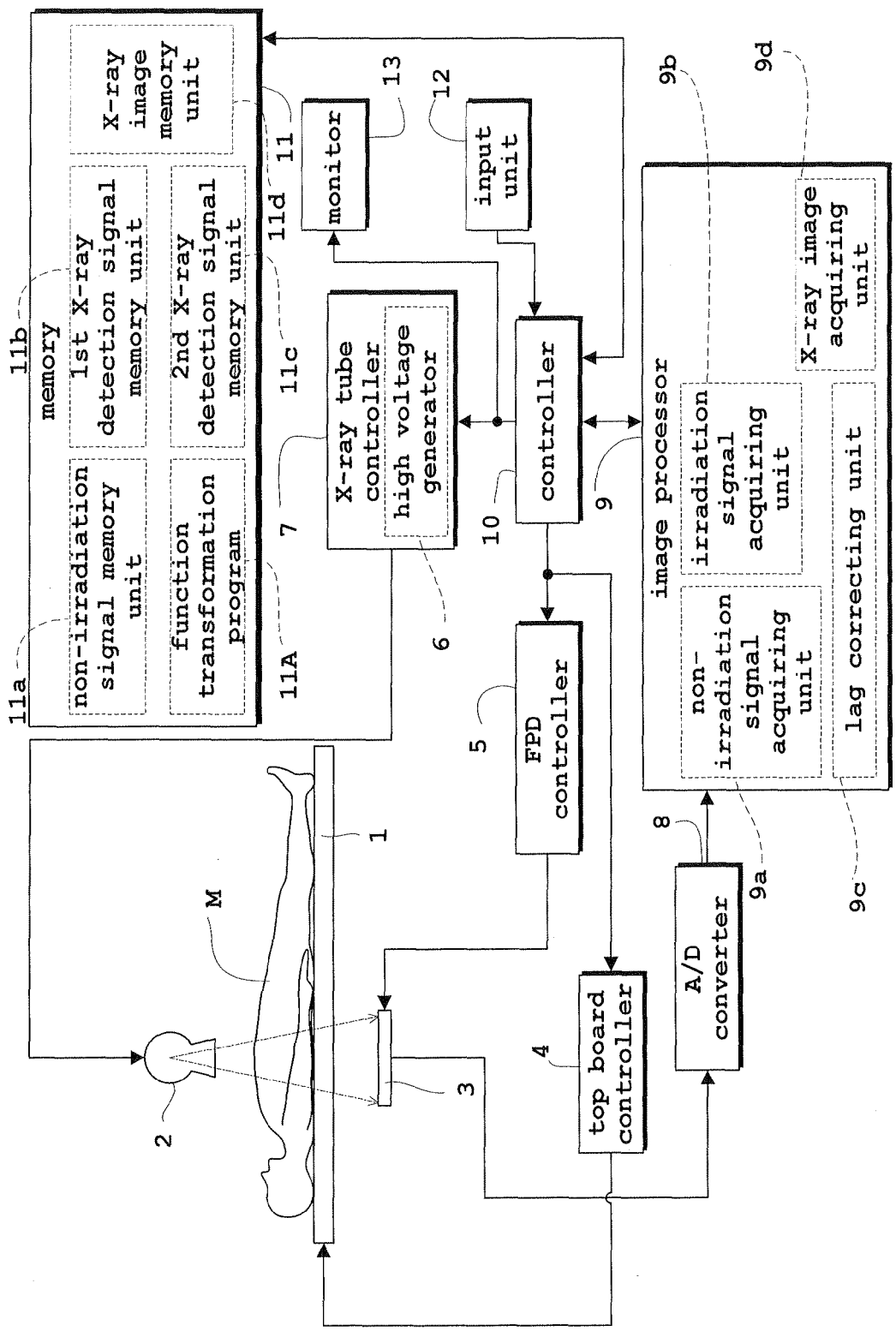
FIG. 1 Block diagram of a fluoroscopic apparatus in each embodiment.
Figure 2:
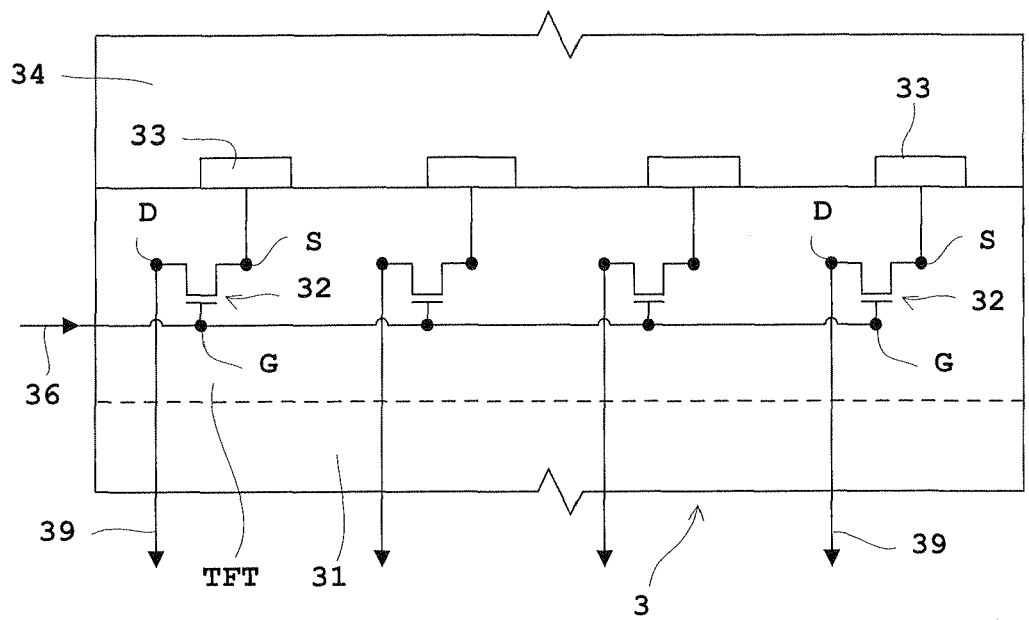
FIG. 2 Equivalent circuit, seen in side view, of a flat panel X-ray detector used in the fluoroscopic apparatus.
Figure 3:
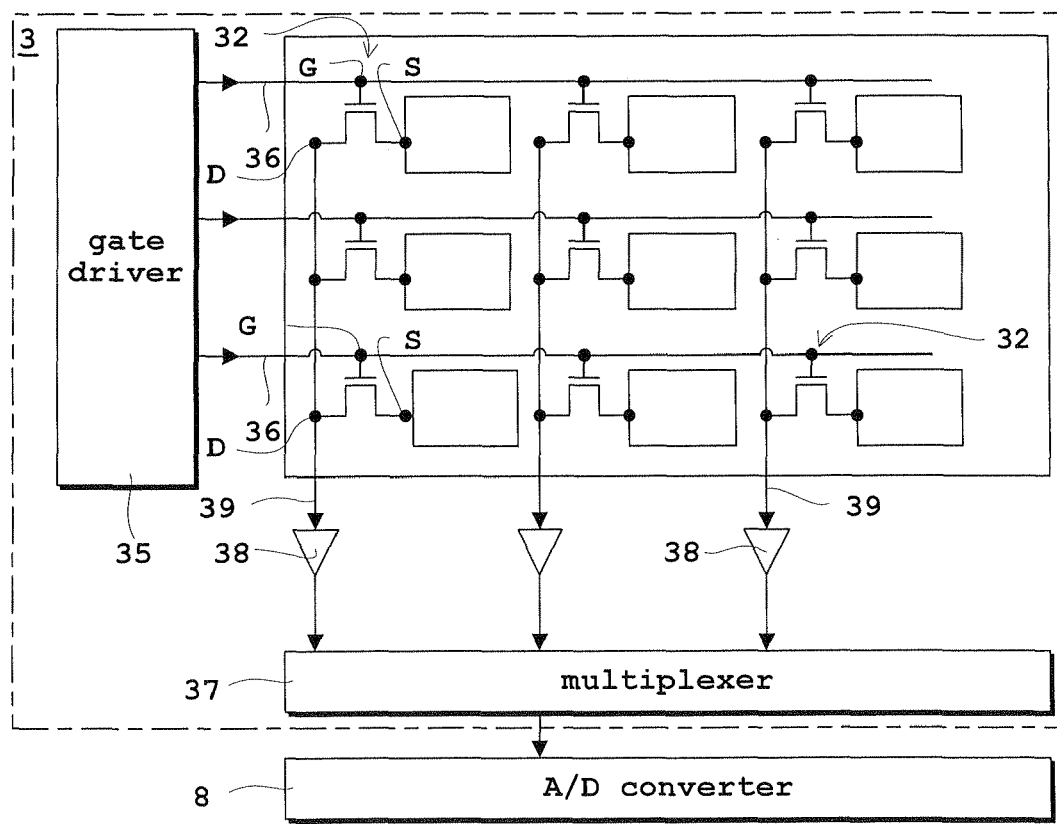
FIG. 3 Equivalent circuit, seen in plan view, of the flat panel X-ray detector.

Embodiment 1 of this invention will be described hereinafter with reference to the drawings. FIG. 1 is a block diagram of a fluoroscopic apparatus in Embodiment 1. FIG. 2 is an equivalent circuit, seen in side view, of a flat panel X-ray detector used in the fluoroscopic apparatus. FIG. 3 is an equivalent circuit, seen in plan view, of the flat panel X-ray detector. Embodiment 1, and also Embodiments 2 and 3 to follow, will be described, taking the flat panel X-ray detector (hereinafter called "FPD" as appropriate) as an example of radiation detection device, and the fluoroscopic apparatus as an example of radiographic apparatus.

As shown in FIG. 1, the fluoroscopic apparatus in Embodiment 1 includes a top board 1 for supporting a patient M, an X-ray tube 2 for emitting X rays toward the patient M, and an FPD 3 for detecting X rays transmitted through the patient M. The X-ray tube 2 corresponds to the radiation emitting device in this invention. The FPD 3 corresponds to the radiation detecting device in this invention.

The fluoroscopic apparatus further includes a top board controller 4 for controlling vertical and horizontal movements of the top board 1, an FPD controller 5 for controlling scanning action of the FPD 3, an X-ray tube controller 7 having a high voltage generator 6 for generating a tube voltage and tube current for the X-ray tube 2, an analog-to-digital converter 8 for fetching charge signals from the FPD 3 and digitizing the charge signals into X-ray detection signals, an image processor 9 for performs various processes based on the X-ray detection signals outputted from the analog-to-digital converter 8, a controller 10 for performing an overall control of these components, a memory 11 for storing processed images, an input unit 12 for the operator to input various settings, and a monitor 13 for displaying the processed images and other information.

The top board controller 4 controls movements of the top board 1, such as moving the top board 1 horizontally to place the patient M in an imaging position, vertically moving and/or rotating the top board 1 to set the patient M to a desired position, horizontally moving the top board 1 during an imaging operation, and horizontally moving the top board 1 to withdraw the patient M from the imaging position after the imaging operation. The FPD controller 5 controls scanning action by moving the FPD 3 horizontally or revolving the FPD 3 about the body axis of patient M. The high voltage generator 6 generates the tube voltage and tube current for the X-ray tube 2, to emit X rays. The X-ray tube controller 7 controls scanning action by moving the X-ray tube 2 horizontally or revolving the X-ray tube 2 about the body axis of patient M, and controls setting of a coverage of a collimator (not shown) disposed adjacent the X-ray tube 2. In time of scanning action, the X-ray tube 2 and FPD 3 are moved while maintaining a mutually opposed relationship, so that the FPD 3 may detect X rays emitted from the X-ray tube 2.

The controller 10 has a central processing unit (CPU) and other elements. The memory 11 has storage media, typically a ROM (Read-Only Memory) and RAM (Random Access Memory). The input unit 12 has a pointing device, typically a mouse, keyboard, joy stick, trackball and/or touch panel. The fluoroscopic apparatus creates images of the patient M, with the FPD 3 detecting X rays transmitted through the patient M, and the image processor 9 performing an image processing based on the X rays detected.

The image processor 9 includes a non-irradiation signal acquiring unit 9a for acquiring a plurality of X-ray detection signals in time of non-irradiation before X-ray irradiation in an imaging event, an irradiation signal acquiring unit 9b for acquiring X-ray detection signals in time of X-ray irradiation in an imaging event, a lag correcting unit 9c for removing lags by applying lag data (i.e. first correction data A in each embodiment) acquired by the non-irradiation signal acquiring unit 9a in time of non-irradiation before a first irradiation described hereinafter, along with first X-ray detection signals and second X-ray detection signals, described hereinafter, acquired by the irradiation signal acquiring unit 9b, and an X-ray image acquiring unit 9d for acquiring an X-ray image by carrying out subtraction using the first X-ray detection signals and second X-ray detection signals resulting from lag-corrected by the lag correcting unit 9c. The lag correcting unit 9c removes lags from the X-ray image by applying both the first X-ray detection signals and second X-ray detection signals to remove any lag-behind parts from the X-ray detection signals, thereby performing lag correction of the lag-behind parts. The non-irradiation signal acquiring unit 9a corresponds to the non-irradiation signal acquiring device in this invention. The irradiation signal acquiring unit 9b corresponds to the irradiation signal acquiring device in this invention. The lag correcting unit 9c corresponds to the lag correcting device in this invention. The X-ray image acquiring unit 9d corresponds to the radiation image acquiring device in this invention.

The memory 11 includes a non-irradiation signal memory unit 11a for storing X-ray detection signals acquired by the non-irradiation signal acquiring unit 9a in time of non-irradiation, a first X-ray detection signal memory unit 11b for storing first X-ray detection signals acquired by the irradiation signal acquiring unit 9b in time of first irradiation, and first X-ray detection signals lag-corrected by the lag correcting unit 9c, a second X-ray detection signal memory unit 11c for storing second X-ray detection signals acquired by the irradiation signal acquiring unit 9b in time of second irradiation, and second X-ray detection signals lag-corrected by the lag correcting unit 9c, and an X-ray image memory unit 11d for storing X-ray images acquired by the X-ray image acquiring unit 9d. In addition, the memory 11 has a function transformation program 11A for transforming the first X-ray detection signals into values (i.e. second correction data B in each embodiment) based on the first X-ray detection signals with a function of the first X-ray detection signals described hereinafter. When performing irradiation twice with a time of non-irradiation in between, the earlier irradiation is regarded as first irradiation, and the later irradiation as second irradiation. The X-ray detection signals acquired by the irradiation signal acquiring unit 9b in time of the first irradiation are regarded as first X-ray detection signals, and the X-ray detection signals acquired by the irradiation signal acquiring unit 9b in time of the second irradiation as second X-ray detection signals.

With the function transformation program 11A provided, the controller 10 reads the function transformation program 11A, and performs transformation with the function of the first X-ray detection signals. The values (i.e. second correction data B in each embodiment) based on the first X-ray detection signals transformed with the function of the first X-ray detection signals are used in the lag correction of the second X-ray detection signals. Thus, the first correction data A corresponds to the lag data based on a plurality of radiation detection signals acquired by the non-irradiation signal acquiring device (or in the non-irradiation signal acquiring step) in time of non-irradiation before the first irradiation in this invention. The second correction data B corresponds to the values based on the first radiation detection signals in this invention.

Figure 6:
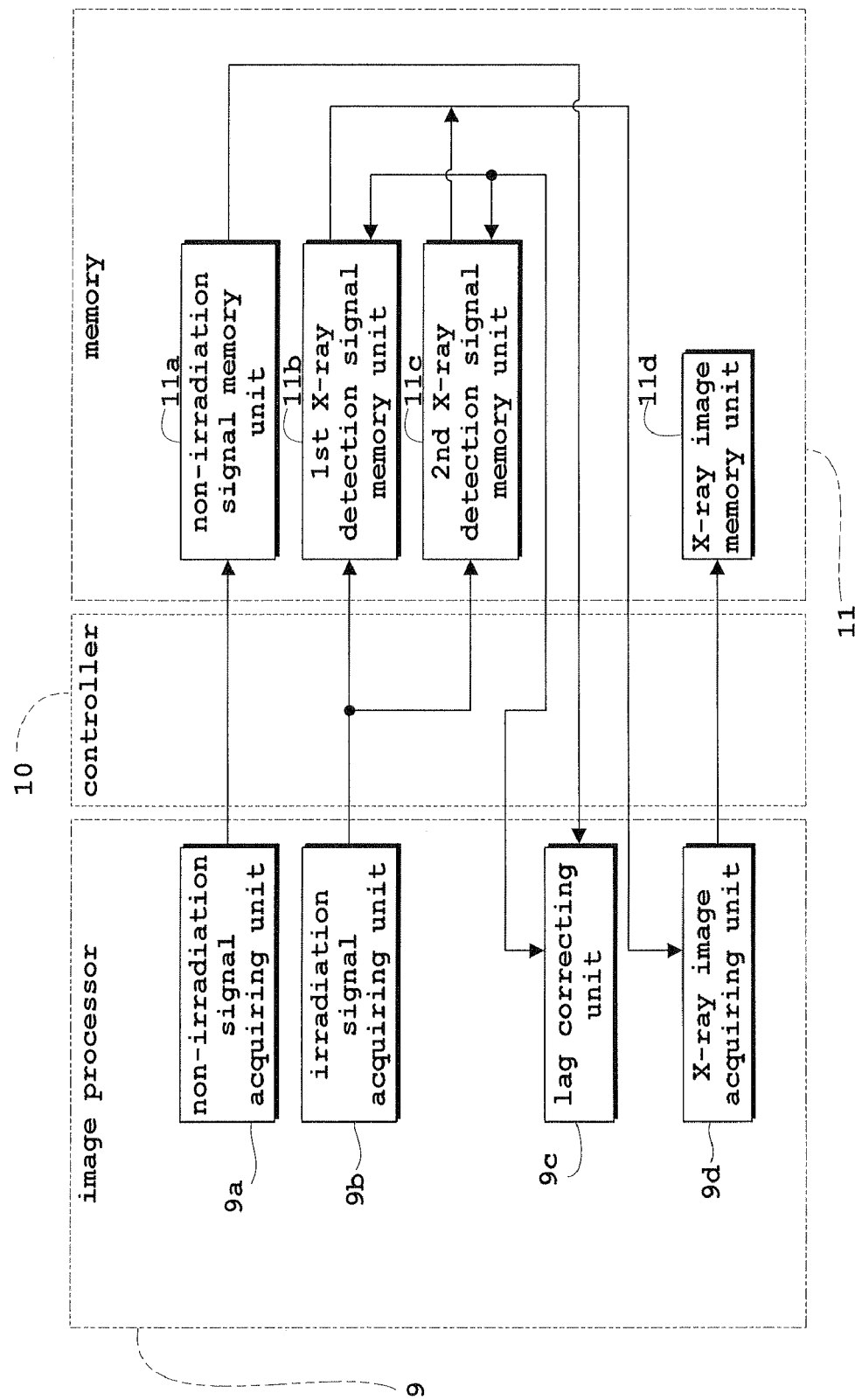
FIG. 6 Schematic view showing flows of data to and from an image processor and a memory in Embodiments 1 and 2.

In Embodiment 1, and also in Embodiment 2 described hereinafter, the lag correcting unit 9c acquires the first correction data which is lag data based on the X-ray detection signals of non-irradiation times read from the non-irradiation signal memory unit 11a (see FIG. 6). Lags are removed by applying the first correction data along with the first X-ray detection signals and second X-ray detection signals. In Embodiment 3 to follow, lag data is obtained by a recursive weighted average (recursive process) as described hereinafter (see FIG. 8).

As shown in FIG. 2, the FPD 3 includes a glass substrate 31, and thin film transistors TFT formed on the glass substrate 31. As shown in FIGS. 2 and 3, the thin film transistors TFT comprise numerous (e.g. 1,024×1,024) switching elements 32 arranged in a two-dimensional matrix of rows and columns. The switching elements 32 are formed separate from one another for respective carrier collecting electrodes 33. Thus, the FPD 3 is also a two-dimensional array radiation detector.

As shown in FIG. 2, an X-ray sensitive semiconductor 34 is laminated on the carrier collecting electrodes 33. As shown in FIGS. 2 and 3, the carrier collecting electrodes 33 are connected to the sources S of the switching elements 32. A plurality of gate bus lines 36 extend from a gate driver 35, and are connected to the gates G of the switching elements 32. On the other hand, as shown in FIG. 3, a plurality of data bus lines 39 are connected through amplifiers 38 to a multiplexer 37 for collecting charge signals and outputting as one. As shown in FIGS. 2 and 3, each data bus line 39 is connected to the drains D of the switching elements 32.

With a bias voltage applied to a common electrode not shown, the gates of the switching elements 32 are turned on by applying thereto (or reducing to 0V) the voltage of the gate bus lines 36. The carrier collecting electrodes 33 output charge signals (carriers) converted from X rays incident on the detection surface through the X-ray sensitive semiconductor 34, to the data bus lines 39 through the sources S and drains D of the switching elements 32. The charge signals are provisionally stored in capacitors (not shown) until the switching elements are turned on. The amplifiers 38 amplify the charge signals read out to the data bus lines 39, and the multiplexer 37 collects the charge signals, and outputs them as one charge signal. The analog-to-digital converter 8 digitizes the outputted charge signal, and outputs it as an X-ray detection signal.

Figure 4:
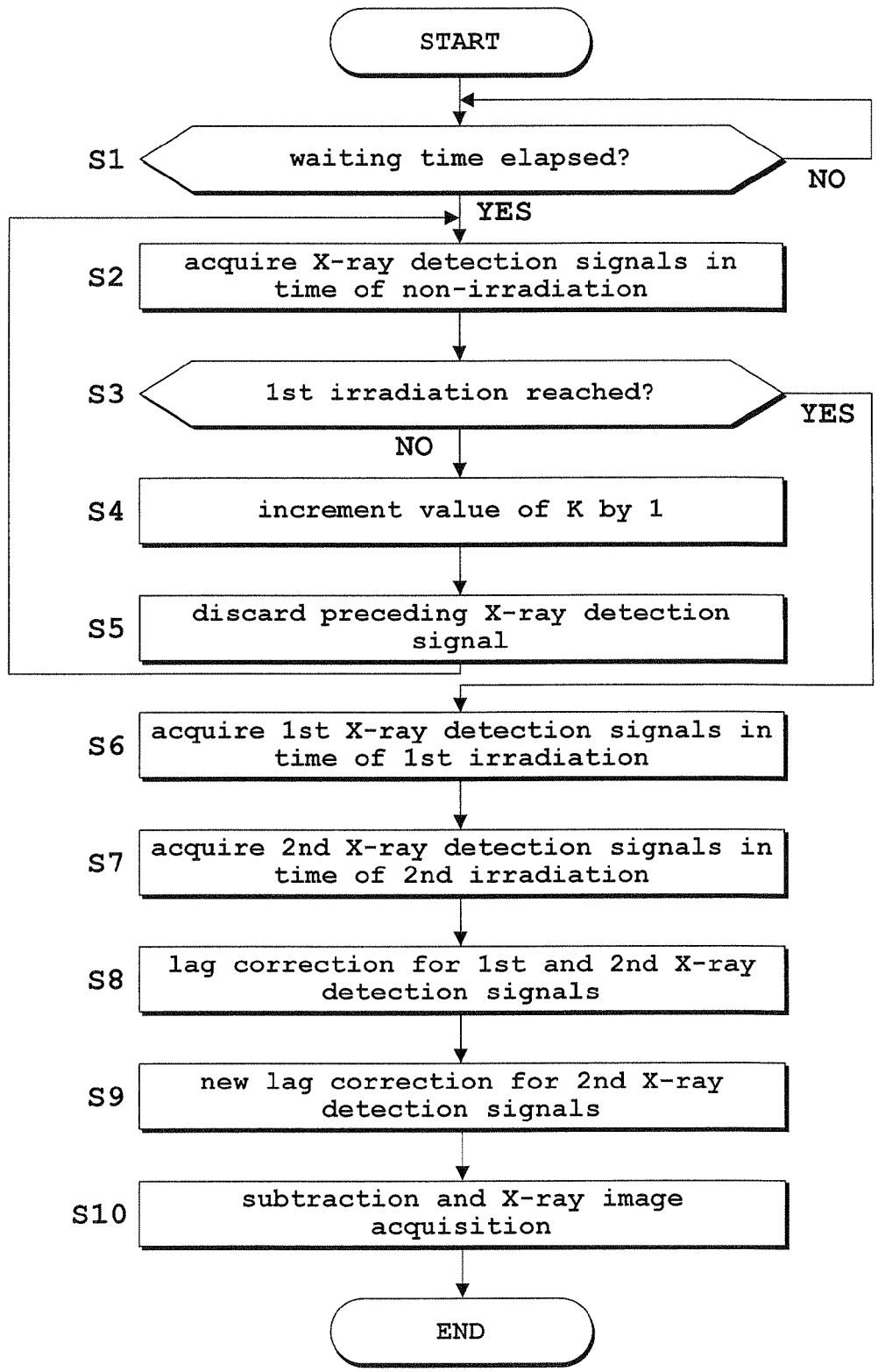
FIG. 4 Flow chart showing a series of signal processing by a non-irradiation signal acquiring unit, an irradiation signal acquiring unit, a lag correcting unit and an X-ray image acquiring unit in Embodiment 1.
Figure 5:
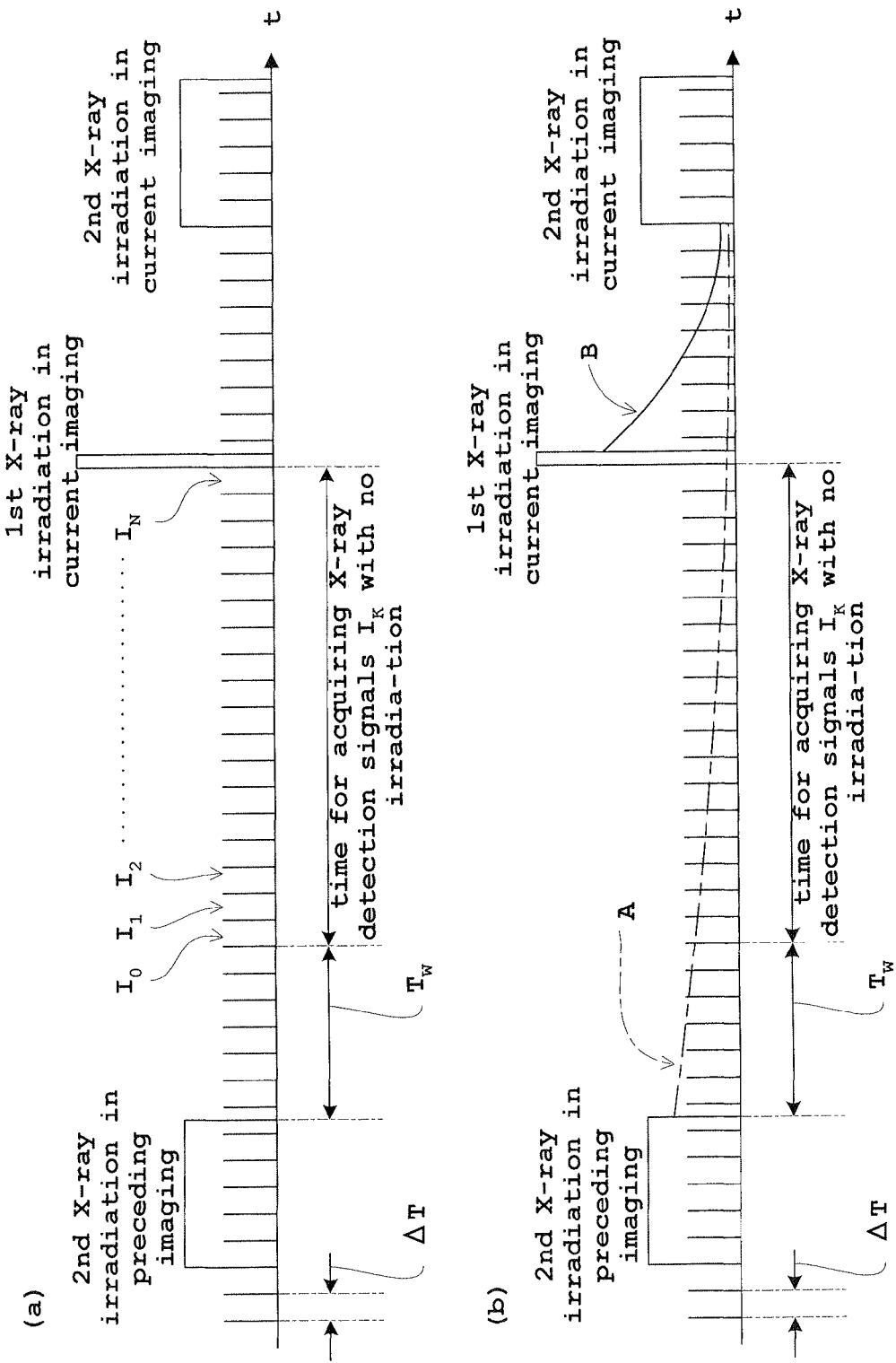
FIG. 5 (a) and (b) are timing charts showing X-ray emissions and acquisition of X-ray detection signals.

Next, a series of signal processing by the non-irradiation signal acquiring unit 9a, irradiation signal acquiring unit 9b, lag correcting unit 9c and X-ray image acquiring unit 9d in Embodiment 1 will be described with reference to the flow chart shown in FIG. 4 and the timing chart shown in FIG. 5. This processing will be described by taking for example what takes place from the end of a second X-ray irradiation in a preceding imaging event through a first X-ray irradiation in a current imaging event to a second X-ray irradiation in the current imaging event.

(Step S1) Waiting Time Elapsed?

A checking is made whether or not a predetermined waiting time $T_W$ has elapsed from the end of second X-ray irradiation in the preceding imaging event as shown in FIG. 5(a). Immediately after the end of irradiation, a lag-behind part includes numerous short time constant components or medium time constant components. These short or medium time constant components attenuate in a short time. After their attenuation, long time constant components become dominant, and remain with substantially the same intensity.

The waiting time $T_W$ is provided so that X-ray detection signals may be acquired in time of non-irradiation after lapse of the predetermined time from the second X-ray irradiation in the preceding imaging event. Upon lapse of the waiting time $T_W$, the operation proceeds to next step S2. Whether the waiting time $T_W$ has passed or not may be determined by means of a timer (not shown). That is, the timer is reset to "0" to start counting simultaneously with the termination of second X-ray irradiation in the preceding imaging event. It may be determined, when a count corresponding to the waiting time $T_W$ is reached, that the waiting time $T_W$ has passed.

The waiting time $T_W$, preferably, is about 15 seconds although this depends on the lag characteristics of individual FPD 3, and the waiting time $T_W$ of about 30 seconds should be sufficient. The longer waiting time $T_W$, e.g. at least 30 seconds, is the better. However, an excessively long time means an extended interval between imaging events. It is realistic for practical purposes to set the waiting time $T_W$ to about 3 seconds.

(Step S2) Acquire X-Ray Detection Signals in Time of Non-Irradiation

The non-irradiation signal acquiring unit 9a successively acquires X-ray detection signals at sampling time intervals $\Delta T$ (e.g. 1/30 sec.) in time of non-irradiation after lapse of the waiting time $T_W$. The number of sampling times before start of the first X-ray irradiation in the current imaging operation is set to (N+1) (note that K=0, 1, 2 ..., N−1 and N), with K=0 indicating the first signal acquired immediately after lapse of the waiting time $T_W$. With a (K+1)th X-ray detection signal regarded as $I_K$, the first X-ray detection signal acquired immediately after lapse of the waiting time $T_W$ is $I_0$, and the X-ray detection signal acquired immediately before start of the first X-ray irradiation in the current imaging event is $I_N$. It is assumed here that steps S2-S5 are successively executed for each sampling time interval $\Delta T$.

(Step S3) First Irradiation Reached?

A checking is made whether or not the time for acquiring X-ray detection signals in step S2, i.e. sampling time, has reached the start of the first X-ray irradiation in the current imaging event (whether or not K=N+1). When it has been reached, the operation jumps to step S6. Otherwise, next step S4 is executed.

(Step S4) Increment Value of K by 1

The value of subscript K is incremented by 1 for a next sampling.

(Step S5) Discard Preceding X-Ray Detection Signal

X-ray detection signal $I_K$ acquired by the non-irradiation signal acquiring unit 9a in step S2 is written and stored in the non-irradiation signal memory unit 11a. At this time, X-ray detection signal $I_{K-1}$ acquired before X-ray detection signal $I_K$ is discarded as no longer necessary.

Thus, only the latest X-ray detection signal remains stored in the non-irradiation signal memory unit 11a. When the operation proceeds to step S5 after incrementing K=0 to K=1 in step S4, there exits no X-ray detection signal preceding signal $I_0$, and thus no signal to be discarded. Then, the operation returns to step S2 for a next sampling, and repeats steps S2-S5 for each sampling time interval $\Delta T$. While, in Embodiment 1, preceding X-ray detection signals are discarded and only the latest X-ray detection signal is retained, it is of course not absolutely necessary to discard the earlier signals. The above steps S2-S5 correspond to the non-irradiation signal acquiring step in this invention.

(Step S6) Acquire First X-Ray Detection Signals in Time of First Irradiation

When step S3 finds the sampling time having reached the first X-ray irradiation in the current imaging event, the (N+1)th X-ray detection signal $I_N$ acquired in step S2 is employed as first correction data A. That is, the lag correcting unit 9c reads X-ray detection signal $I_N$ acquired just before the start of the first X-ray irradiation in the current imaging event from the non-irradiation signal memory unit 11a, and acquires the X-ray detection signal $I_N$ as first correction data A. The first correction data A becomes $A=I_N$. The first correction data A acquired by the lag correcting unit 9c is applied to the first X-ray detection signals and second X-ray detection signals in step S8 as described hereinafter. In parallel with the acquisition of the first correction data A, the first irradiation is carried out by emitting X rays at 120 kV for 10 ms. Upon completion of the first X-ray irradiation in the current imaging event, the first X-ray detection signals acquired in time of the first irradiation are written and stored in the first irradiation signal memory unit 11b. This step S6 corresponds to the first irradiation signal acquiring step in this invention.

(Step S7) Acquire Second X-Ray Detection Signals in Time of Second Irradiation

The second irradiation is carried out immediately upon completion of the first irradiation in step S6. In practice, an idle time of about 200 ms occurs between the first irradiation and second irradiation due to the functional limitation of the apparatus. The second irradiation is carried out by emitting X rays at 60 kV for 50 to 100 ms. Upon completion of the second X-ray irradiation in the current imaging event, the second X-ray detection signals acquired in time of the second irradiation are written and stored in the second irradiation signal memory unit 11c. This step S7 corresponds to the second irradiation signal acquiring step in this invention.

(Step S8) Lag Correction for the First and Second X-Ray Detection Signals

The lag correcting unit c carries out lag correction for the first and second X-ray detection signals by applying the first correction data A acquired in step S6 to both the first X-ray detection signals read from the first X-ray detection signal memory unit 11b and the second X-ray detection signals read from the second X-ray detection signal memory unit 11c. In each embodiment, the lag correction is carried out by subtracting the first correction data A from the first and second X-ray detection signals for each pixel, respectively. Assuming that the first X-ray detection signals are $I_{FIRST}$, the second X-ray detection signals $I_{SECOND}$, the first X-ray detection signals after the lag correction $I'_{FIRST}$, and the second X-ray detection signals after the lag correction $I'_{SECOND}$, the first X-ray detection signals $I'_{FIRST}$ after the lag correction become $I'_{FIRST}=I_{FIRST}-A$, and the second X-ray detection signals $I'_{SECOND}$ after the lag correction become $I'_{SECOND}=I_{SECOND}-A$. The first X-ray detection signals after the lag correction $I'_{FIRST}$ also are written and stored in the first irradiation signal memory unit 11b again, and the second X-ray detection signals after the lag correction $I'_{SECOND}$ also are written and stored in the second irradiation signal memory unit 11c again.

In practice, the timing of the first X-ray irradiation in the current imaging event is not necessarily determined beforehand. Therefore, the timing of reaching K=N+1 is not necessarily known beforehand, either. Thus, in practice, the foregoing steps S2-S5 are repeated for each sampling time interval ΔT, and the sampling time reaching the start of the first X-ray irradiation in the current imaging event in step S3 is regarded as reaching K=N+1. Of course, where the timing of the first X-ray irradiation in the current imaging event is determined beforehand, the timing of reaching K=N+1 is also known beforehand. Thus, a value of N may be determined beforehand, and the sampling time may be set to reach the start of the first X-ray irradiation in the current imaging event in accordance with the timing of reaching K=N+1. Step S8 corresponds to the lag correcting step in this invention.

(Step S9) New Lag Correction for the Second X-Ray Detection Signals

As noted above, the second irradiation is carried out immediately upon completion of the first irradiation. Therefore, X-ray detection signals in time of non-irradiation for lag correction are not acquired between the first irradiation (step S6) and second irradiation (step S7). As shown in FIG. 5(b), the lag components before the first X-ray irradiation in the current imaging event are superimposed as the first correction data A, and the lag components before the second X-ray irradiation in the current imaging event are regarded as being superimposed as second correction data B including the lag components resulting from the first irradiation as well as the first correction data A. That is, the second X-ray detection signals acquired in step S7 are regarded as including the lag components (second correction data B here) due to the first X-ray detection signals acquired in step S6. Thus, a new lag correction is carried out for the second X-ray detection signals to remove lags from the second X-ray detection signals by using the second correction data B which are values based on the first X-ray detection signals. In each embodiment, the second correction data B which are values based on the first X-ray detection signals are expressed by the function of the first X-ray detection signals $I'_{FIRST}$ after the lag correction in step S8, and a new lag correction is carried out for the second X-ray detection signals using the second correction data B, by subtracting the second correction data B from the second X-ray detection signals $I'_{SECOND}$ after the lag correction in step S8. Specifically, where the function is F, and the second X-ray detection signals after the further, second lag correction is $I''_{SECOND}$, the second correction data B is derived from the following equation (2), and the second X-ray detection signals $I''_{SECOND}$ are derived from the following equation (3):

$$B=F(I'_{FIRST}) \qquad (2)$$

$$I''_{SECOND}=I'_{SECOND}-B \qquad (3)$$

In carrying out function transformation by equation (2) above, the function transformation program 11A noted hereinbefore is executed. A specific method of determining the function will be summarized herein after Embodiment 3. The second X-ray detection signals $I''_{SECOND}$ after the further, second lag correction are also written and stored in the second X-ray detection signal memory unit 11c again.

(Step S10) Subtraction and X-Ray Image Acquisition

The X-ray image acquiring unit 9d acquires an X-ray image by carrying out subtraction using the first X-ray detection signals $I'_{FIRST}$ after the lag correction in step S6 and the second X-ray detection signals $I''_{SECOND}$ after the further, second lag correction in step S9. The X-ray image acquired by the X-ray image acquiring unit 9d is written and stored in the X-ray image memory unit 11d. Regarding the subtraction, $I'_{FIRST}$ may be substituted for $I_1$ in equation (1) above, and $I''_{SECOND}$ for $I_2$, to obtain an energy subtraction image $I_{DES}$, the energy subtraction image $I_{DES}$ serving as the X-ray image. The subtraction is not limited to equation (1) above, but subtraction may be performed between respective logarithms as in Patent Documents 3-6 noted hereinbefore. This step S10 corresponds to the radiographic image acquiring step in this invention. The X-ray image corresponds to the radiographic image serving an intended purpose in this invention.

According to Embodiment 1 having the described construction, steps S2-S5 are executed to acquire a plurality of X-ray detection signals ($I_0, I_1, I_2, \ldots, I_{N-1}, I_N$ in Embodiment 1) in time of non-irradiation before X-ray irradiation in an imaging event, and step S6 is executed to acquire X-ray detection signals in time of the first irradiation which is an X-ray irradiation time in the imaging event after the above steps S2-S5. Further, in step S7, X-ray detection signals are acquired in time of the second irradiation which is an irradiation time of radiation in the imaging event, with non-irradiation inserted after the above step S6. In step S8, lag data (first correction data A) based on these X-ray detection signals acquired in steps S2-S5 is applied to both the first X-ray detection signals $I_{FIRST}$ which are the X-ray detection signals acquired in step S6, and the second X-ray detection signals $I_{SECOND}$ which are the X-ray detection signals acquired in step S7, to carry out lag correction about the lag-behind parts by removing the lag-behind parts included in the X-ray detection signals from the X-ray detection signals. In step S10, an X-ray image is acquired by carrying out subtraction using the first X-ray detection signals $I'_{FIRST}$ and second X-ray detection signals $I''_{SECOND}$ for which lag correction has been carried out in step S8.

Thus, there is no need to carry out lag correction by performing recursive computations corresponding in number to the number of times of sampling to acquire X-ray detection signals as performed in Patent Document 2 noted hereinbefore. Further, since lag correction is carried out by applying lag data (first correction data A) based on the plurality of X-ray detection signals acquired in steps S2-S5 before the first irradiation, to both the first and second X-ray detection signals, respectively, lag correction is possible without acquiring lag components between the first irradiation and second irradiation. Therefore, also in the case of carrying out X-ray irradiation twice (first irradiation and second irradiation) for one image, lag-behind parts included in the X-ray detection signals can be removed simply from the X-ray detection signals. It is also not necessary to use backlight as in Patent Document 1 noted hereinbefore, and thus the construction of the apparatus is not complicated.

As noted above, the second X-ray detection signals acquired in step S7 are considered to include lag components (second correction data B) attributable to the first X-ray detection signals acquired in step S6. It is thus desirable, as in Embodiment 1 and also in Embodiments 2 and 3 described hereinafter, to carry out a further lag correction for the second X-ray detection signals, as in step S9, to remove lags from the second X-ray detection signals by using values (second correction data B) based on the first X-ray detection signals. Also in carrying out a further lag correction for the second X-ray detection signals, the lag correction for the second X-ray detection signals is possible by using the values (second correction data B) based on the first X-ray detection signals, without acquiring lag components between the first irradiation and second irradiation.

In Embodiment 1, and also in Embodiments 2 and 3 to follow, a plurality of X-ray detection signals are acquired in time of non-irradiation after lapse of the predetermined time (i.e. the waiting time $T_W$ in Embodiment 1) from the second X-ray irradiation in a preceding imaging event. Consequently, a plurality of X-ray detection signals are acquired in time of non-irradiation before the first X-ray irradiation in a current imaging event. When the second X-ray irradiation in the preceding imaging event is completed and a transition is made to a state of non-irradiation, short time constant components or medium time constant components of a lag-behind part attenuate in a short time. After their attenuation, long time constant components become dominant, and remain with substantially the same intensity. Consequently, when X-ray detection signals are acquired immediately after completion of the second X-ray irradiation in the preceding imaging event, short and medium time constant components are included in the signals acquired. The lag-behind parts having the short and medium time constant components cannot be eliminated from the signals accurately. Thus, in Embodiment 1, a plurality of X-ray detection signals are acquired in time of non-irradiation after lapse of the predetermined time from the second X-ray irradiation in the preceding imaging event. A plurality of X-ray detection signals are acquired in time of non-irradiation after lapse of the predetermined time from the first X-ray irradiation in the current imaging event. Consequently, a plurality of X-ray detection signals are acquired in time of non-irradiation before the first X-ray irradiation in the current imaging event. The signals may be acquired in a state of including only the long time constant components which remain after lapse of the predetermined time. The signals are free from the short and medium time constant components, and a lag-behind part having the long time constant components may be eliminated accurately.

EMBODIMENT 2

Next, Embodiment 2 of this invention will be described with reference to the drawings. Like reference signs will be used to identify like parts which are the same as in Embodiment 1 and will not be described again. A fluoroscopic apparatus in Embodiment 2 is similar to the apparatus in Embodiment 1, and only the series of signal processing by the non-irradiation signal acquiring unit $9a$, irradiation signal acquiring unit $9b$, lag correcting unit $9c$ and X-ray image acquiring unit $9d$ is different from that in Embodiment 1.

Figure 7:
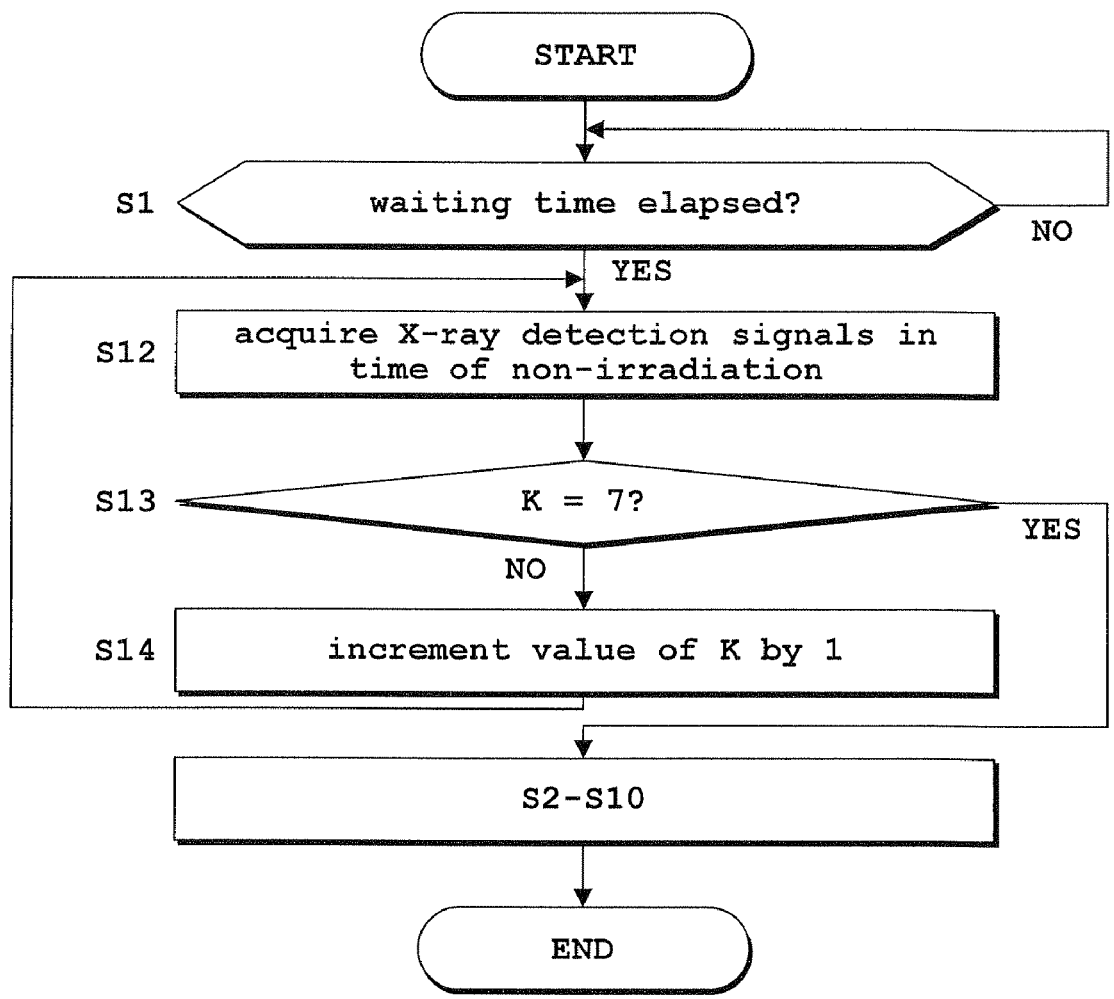
FIG. 7 Flow chart showing a series of signal processing by a non-irradiation signal acquiring unit, an irradiation signal acquiring unit, a lag correcting unit and an X-ray image acquiring unit in Embodiment 2.

The series of signal processing by the non-irradiation signal acquiring unit $9a$, irradiation signal acquiring unit $9b$, lag correcting unit $9c$ and X-ray image acquiring unit $9d$ in Embodiment 2 will be described with reference to the flow chart of FIG. 7. Like numerals are affixed to like steps in Embodiment 1 and will not be described again.

(Step S1) Waiting Time Elapsed?

As in Embodiment 1 described hereinbefore, a checking is made whether or not the waiting time $T_W$ has elapsed from the end of the second X-ray irradiation in the preceding imaging event. Upon lapse of the waiting time $T_W$, the operation proceeds to next step S12.

(Step S12) Acquire X-Ray Detection Signals in Time of Non-Irradiation

As in Embodiment 1 described hereinbefore, X-ray detection signals are successively acquired at sampling time intervals $\Delta T$ (e.g. $\frac{1}{30}$ second) in time of non-irradiation after lapse of the waiting time $T_W$. In Embodiment 2, as will become clear from the following description, the signals from the first X-ray detection signal $I_0$ acquired immediately after the waiting time $T_W$ to the seventh X-ray detection signal $I_6$ remain stored in the non-irradiation signal memory unit $11a$, instead of being discarded, until acquisition of the eighth X-ray detection signal $I_7$ (i.e. K=7). It is to be noted that steps S12-S14 are repeated at each of the sampling time intervals $\Delta T$.

(Step S13) K=7?

A checking is made whether or not subscript K has reached 7 (i.e. K=7), that is whether the sampling time has reached to the eighth. When K=7, the operation jumps to step S2. Otherwise, next step S14 is executed.

(Step S14) Increment Value of K by 1

As in Embodiment 1 described hereinbefore, the value of subscript K is incremented by 1 for a next sampling. X-ray detection signals $I_K$ acquired by the non-irradiation signal acquiring unit 9a in step S12 are successively written and stored in the non-irradiation signal memory unit 11a until acquisition of the eighth X-ray detection signal $I_7$ (i.e. K=7). At this time, X-ray detection signal $I_{K-1}$ acquired before X-ray detection signal $I_K$ is not discarded but is retained in the non-irradiation signal memory unit 11a until eight X-ray detection signals accumulate in the non-irradiation signal memory unit 11a. Then, the operation returns to step S12 for a next sampling, and repeats steps S12-S14 for each of the sampling time intervals ΔT.

(Step S2)-(Step S10)

When the sampling time has reached the start of the first X-ray irradiation for the current imaging event in step S13, steps S2-S8 similar to Embodiment 1 are executed. However, eight X-ray detection signals are constantly stored in the non-irradiation signal memory unit 11a, and when the latest X-ray detection signal is newly stored in the non-irradiation signal memory unit 11a in step S5, the oldest X-ray detection signal only is discarded. When the sampling time has reached the start of the first X-ray irradiation in the current imaging event in step S3, the first correction data is obtained based on the eight signals from (N−6)th X-ray detection signal $I_{N-7}$ to (N+1)th X-ray detection signal $I_N$ acquired in step S2. Specifically, the first correction data is derived from an average of these signals ($A = \Sigma I_i/8$, where Σ is a total of i=N−7 to N). The process from acquisition of the first X-ray detection signals in time of the first irradiation carried out in parallel with the acquisition of the first correction data A to the subtraction and acquisition of an X-ray image is the same as in Embodiment 1, and its description is omitted.

According to Embodiment 2 having the described construction, as in Embodiment 1, the following takes place when carrying out lag correction for the lag-behind parts by removing the lag-behind parts included in the detected X-ray detection signals from the X-ray detection signals. A plurality of X-ray detection signals ($I_0, I_1, I_2, \ldots, I_{N-1}, I_N$ in Embodiment 2) are acquired in time of non-irradiation before X-ray irradiation in an imaging event. In step S8, lag data (first correction data A) based on these X-ray detection signals is applied to both the first X-ray detection signals $I_{FIRST}$ which are the X-ray detection signals acquired in step S6, and the second X-ray detection signals $I_{SECOND}$ which are the X-ray detection signals acquired in step S7, to carry out lag correction about the lag-behind parts by removing the lag-behind parts included in the X-ray detection signals from the X-ray detection signals. An X-ray image is acquired by carrying out subtraction using the first X-ray detection signals $I'_{FIRST}$ and second X-ray detection signals $I''_{SECOND}$ for which lag correction has been carried out. Thus, lag correction is possible without acquiring lag components between the first irradiation and second irradiation. Therefore, also in the case of carrying out X-ray irradiation twice (first irradiation and second irradiation) for one image, lag-behind parts included in the X-ray detection signals can be removed simply from the X-ray detection signals.

In Embodiment 1, random noise components of the first X-ray detection signals $I'_{FIRST}$ after the lag correction become 2½ times those of $I'_{FIRST}$, thereby lowering the signal-to-noise ratio by 41% ($=(2^{1/2}-1)$). In order to suppress this deterioration, Embodiment 2, as distinct from Embodiment 1, derives the first correction data A by directly using the plurality of X-ray detection signals ($I_{N-7}, I_{N-6}, \ldots, I_{N-1}$ and $I_N$ in Embodiment 2). In this case, the random noise components of X-ray detection signals $I'_{FIRST}$ after the lag correction cause deterioration no more than 6% of the X-ray detection signals $I_{FIRST}$ before the correction. Thus, the lag correction can be effected without lowering the signal-to-noise ratio. Random noise components of the second X-ray detection signals $I'_{SECOND}$ after the lag correction are similar to the random noise components of the first X-ray detection signals $I'_{FIRST}$ after the lag correction.

In Embodiment 2, the first correction data A is obtained by directly using eight X-ray detection signals. However, the invention is not limited to a particular number of X-ray detection signals to be used. Further, although the first correction data A is derived from an average of the signals, the first correction data A may be derived from a median. A histogram showing intensities of the signals may be formed, to derive a mode as first correction data A from the histogram. Thus, the invention is not limited to a particular way of deriving the lag data (first correction data A) based on the radiation detection signals (X-ray detection signals) acquired in time of non-irradiation.

EMBODIMENT 3

Figure 8:
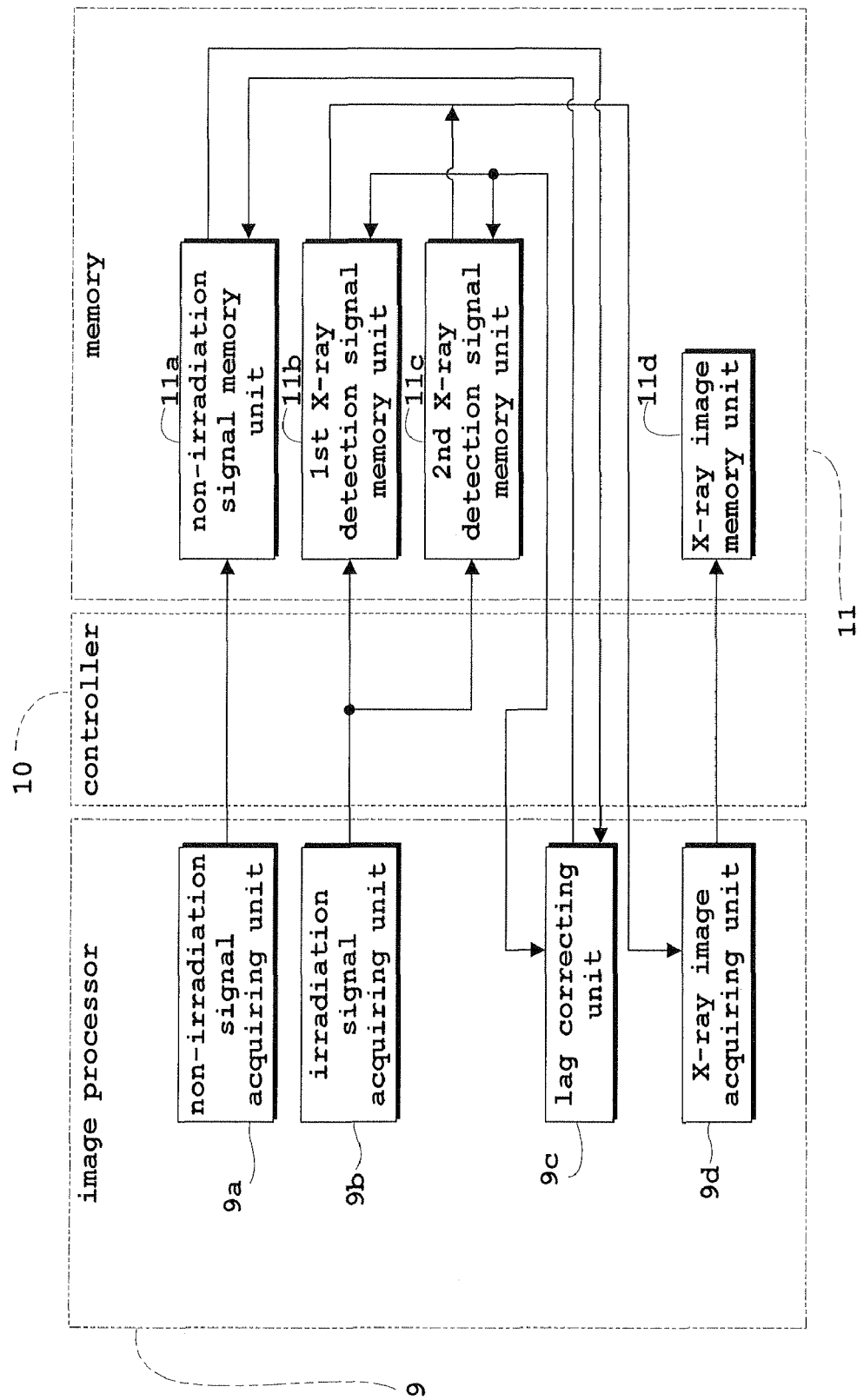
FIG. 8 Schematic view showing flows of data to and from an image processor and a memory in Embodiment 3.

Next, Embodiment 3 of this invention will be described with reference to the drawings. FIG. 8 is a schematic view showing flows of data to and from an image processor 9 and a memory 11 in Embodiment 3. Like reference signs will be used to identify like parts which are the same as in Embodiments 1 and 2, and will not be described again. A fluoroscopic apparatus in Embodiment 3 is the same as the apparatus in Embodiments 1 and 2, except the flows of data to and from the image processor 9 and memory 11 shown in FIG. 8. The series of signal processing by the non-irradiation signal acquiring unit 9a, irradiation signal acquiring unit 9b, lag correcting unit 9c and X-ray image acquiring unit 9d also is different from those in Embodiments 1 and 2.

In Embodiment 3, as shown in FIG. 8, the lag correcting unit 9c acquires lag data (first correction data A in each embodiment) by recursive computation based on the X-ray detection signals in time of non-irradiation read from the non-irradiation signal memory unit 11a. The acquisition of the first correction data A by recursive computation will be described with reference to the flow chart of FIG. 9. This embodiment is the same as Embodiments 1 and 2 described hereinbefore, in that the lag correcting unit 9c removes lags by applying the first correction data A to both the first X-ray detection signals and second X-ray detection signals, and that the X-ray image acquiring unit 9d acquires an X-ray image by performing subtraction using the first X-ray detection signals and second X-ray detection signals both resulting from the lag correction by the lag correcting unit 9c.

Figure 9:
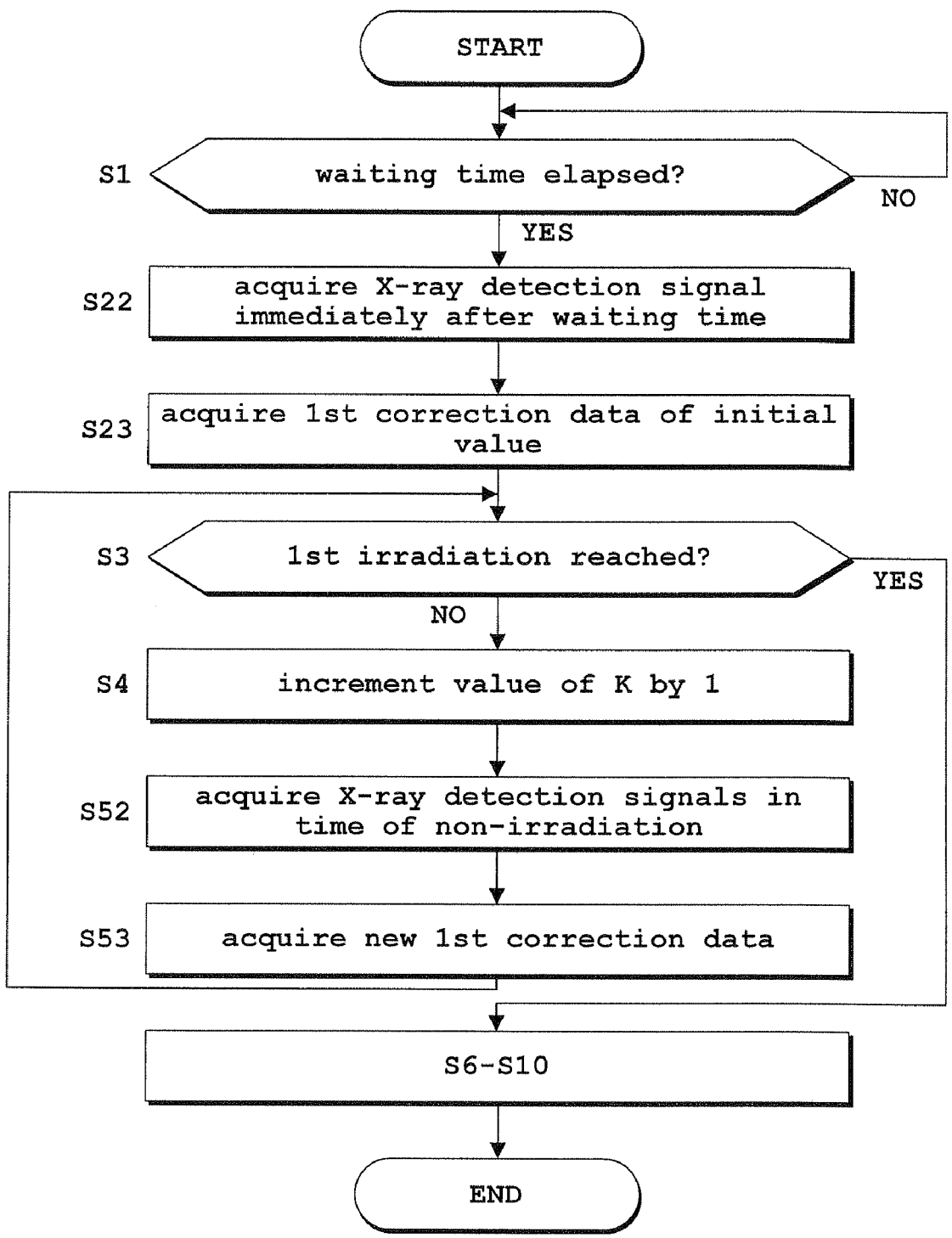
FIG. 9 Flow chart showing a series of signal processing by a non-irradiation signal acquiring unit, an irradiation signal acquiring unit, a lag correcting unit and an X-ray image acquiring unit in Embodiment 3.

Next, the series of signal processing by the non-irradiation signal acquiring unit 9a, irradiation signal acquiring unit 9b, lag correcting unit 9c and X-ray image acquiring unit 9d in Embodiment 3 will be described with reference to the flow chart of FIG. 9. Like numerals are affixed to like steps in Embodiments 1 and 2 and will not be described again.

(Step S1) Waiting Time Elapsed?

As in Embodiments 1 and 2 described hereinbefore, a checking is made whether or not the waiting time $T_W$ has elapsed from the end of the second X-ray irradiation in the preceding imaging event. Upon lapse of the waiting time $T_W$, the operation proceeds to next step S22.

(Step S22) Acquire X-Ray Detection Signals Immediately After Waiting Time

As in Embodiments 1 and 2 described hereinbefore, X-ray detection signals are successively acquired at sampling time intervals ΔT (e.g. 1/30 second) in time of non-irradiation after lapse of the waiting time $T_W$. A first X-ray detection signal $I_0$ is acquired immediately after the waiting time $T_W$, which is written and stored in the non-irradiation signal memory unit 11a.

(Step S23) Acquire First Correction Data of Initial Value

The lag correcting unit 9c reads this X-ray detection signal $I_0$ from the non-irradiation signal memory unit 11a, and acquires the X-ray detection signal $I_0$ as first correction data $A_0$ which is an initial value of the first correction data A.

(Step S3)-(Step S4)

After the first correction data $A_0$ of initial value is acquired in step S23, steps S3 and S4 similar to Embodiment 1 are executed.

(Step S52) Acquire X-Ray Detection Signals in Time of Non-Irradiation

As in Embodiments 1 and 2 described hereinbefore, X-ray detection signals are successively acquired at sampling time intervals ΔT (e.g. 1/30 sec.) in time of non-irradiation after lapse of the waiting time $T_W$. However, the X-ray detection signals acquired in time of non-irradiation in step S52 in Embodiment 3 are a second X-ray detection signal $I_1$ and subsequent signals.

(Step S53) Acquisition of New First Correction Data

When acquiring new first correction data of the second et seq., an (N+1)th first correction data $A_N$ is derived by recursive computation from the X-ray detection signal $I_N$ in time of non-irradiation and the preceding first correction data $A_{N-1}$. In Embodiment 3, the first correction data $A_N$ is derived by a recursive weighted average (hereinafter referred to as "recursive process" as appropriate) from the following equation (4):

$$A_N = (1-P) \times A_{N-1} + P \times I_N \qquad (4)$$

In this process, $I_0 = A_0$ as noted above. P is a load ratio which takes a value of 0 to 1.

To acquire next first correction data $A_K$, the operation returns to step S3 for carrying out the recursive process of equation (4) above. When the first X-ray irradiation in the current imaging event is reached in step S3, the first correction data $A_N$ acquired in step S53 immediately before step S3 serves as the latest data. The latest first correction data $A_N$ is acquired as correction data A.

(Step S6)-(Step S10)

The process from acquisition of the first X-ray detection signals in time of the first irradiation in step S6 to the subtraction and acquisition of an X-ray image in step S10 is the same as in Embodiment 1, and its description is omitted.

According to Embodiment 3 having the described construction, as in Embodiments 1 and 2 described hereinbefore, lag correction is carried out for the lag-behind parts by applying the acquired first correction data A to both the first X-ray detection signals $I_{FIRST}$ and second X-ray detection signals $I_{SECOND}$ to remove the lag-behind parts included in the X-ray detection signals from the X-ray detection signals. An X-ray image is acquired by carrying out subtraction using the first X-ray detection signals $I'_{FIRST}$ and second X-ray detection signals $I''_{SECOND}$ for which lag correction has been carried out. Thus, lag correction is possible without acquiring lag components between the first irradiation and second irradiation. Therefore, also in the case of carrying out X-ray irradiation twice (first irradiation and second irradiation) for one image, lag-behind parts included in the X-ray detection signals can be removed simply from the X-ray detection signals.

In Embodiment 3, a plurality of X-ray detection signals are successively acquired at sampling time intervals delta-T (e.g. 1/30 second) in time of non-irradiation. Assuming a certain point in time of non-irradiation to be the (N+1)th, the first correction data A is obtained based on a plurality of X-ray detection signals including the (N+1)th signal so far acquired successively. That is, an (N+1)th first correction data $A_N$ is obtained. For this purpose, the recursive computation is repeated based on the X-ray detection signal $I_N$ acquired at the (N+1)th point of time, and the first correction data A based on a plurality of X-ray detection signals successively acquired up to the Nth point of time before the (N+1)th point of time, that is the first correction data $A_{N-1}$ before the first correction data $A_N$.

In Embodiment 3, the first correction data is obtained by recursive process (see equation (4) above) which is a recursive weighted average as recursive computation. This realizes a lag correction based on the first correction data with increased reliability.

[Determination of Function]

Figure 10:
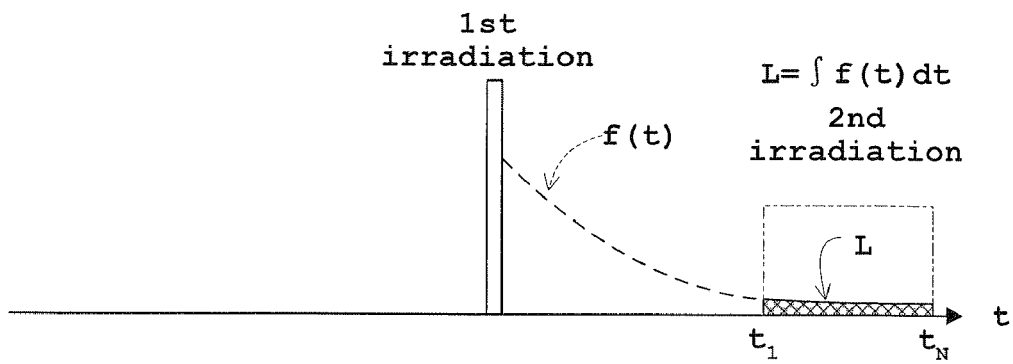
FIG. 10 Explanatory view schematically showing a lag of a first irradiation for determining, in advance, a function of first X-rays detection signals representing second correction data in each embodiment.
Figure 11:
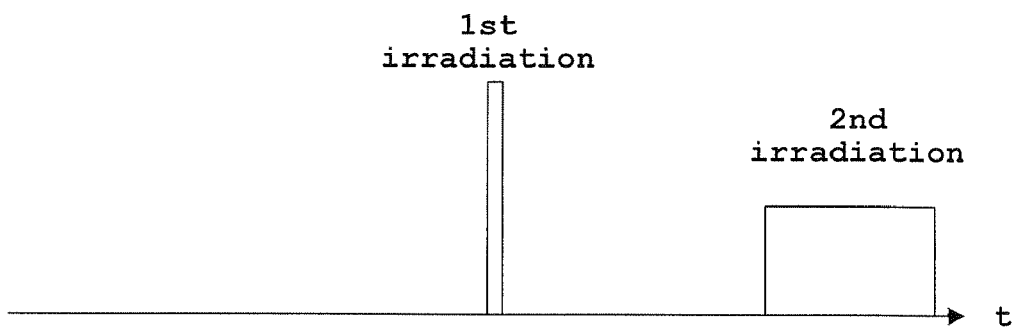
FIG. 11 Timing chart of emitting X rays twice for one image.
Figure 12:
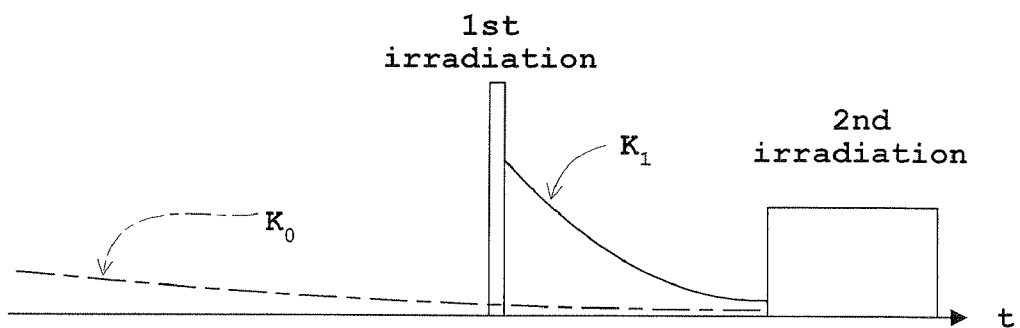
FIG. 12 Timing chart of superimposing lag components on FIG. 11.

Next, a specific method of determining function F used for the second correction data B in each embodiment will be described. FIG. 10 is an explanatory view schematically showing a lag of the first irradiation for determining beforehand the function F of the first X-ray detection signals representing the second correction data B in each embodiment.

Function F of the first X-ray detection signals may be determined from information on X-ray detection acquired before a series of X-ray detection signals, acquiring conditions before the series of X-ray detection signals, or peculiar information on the flat panel type X-ray detector (FPD) 3 that detects X rays. More particularly, intensity of X-ray detection signals acquired before shipment of FPD 3 is an example of information on X-ray detection acquired before the series of X-ray detection signals. A time between the first irradiation and second irradiation is an example of acquiring conditions before the series of X-ray detection signals. The peculiar information on FPD 3 may, for example, be obtained before shipment for each FPD 3 used, under the acquiring condition shown in FIG. 10.

As shown in FIG. 10, a first irradiation is carried out as in an actual imaging event before shipment. At this time, a second irradiation is not carried out. Assume that a second irradiation also is carried out before shipment, an irradiation time for the second irradiation corresponds to the time $t_1-t_N$ shown in the two-point chain line in FIG. 10. When the first irradiation is completed, lag components resulting from the first irradiation remain until the time of the second irradiation which should occur normally, while attenuating as shown in a dotted line in FIG. 10. These lag components are termed f(t) as shown in FIG. 10. Then, when the lag due to the first irradiation is termed L, lag L due to the first irradiation can be regarded as a value for the second irradiation of f(t) integrated with time $t_1-t_N$ (see the hatching in FIG. 10) (see the following equation (5)).

$$L = \int f(t) dt \qquad (5)$$

However, ∫ is an integral with time $t_1-t_N$. If function F is determined to reduce the lag due to the first irradiation to 0, the lag components due to the first X-ray detection signals acquired by the first X-ray irradiation in the current imaging event after shipment may be removed by conversion to second correction data B with function F of the first X-ray detection signals, and subtracting the second correction data B as in equation (3) above. In order to determine function F to reduce the lag due to the first irradiation to 0, function F is determined such that function F of the first X-ray detection signals S becomes equal to lag L due to the first irradiation as in the following equation (6), where the first X-ray detection signals acquired by the first irradiation before shipment are S:

$$F(S)=L \qquad (6)$$

To summarize the above, a first irradiation is carried out before shipment, without carrying out a second irradiation, lag L due to the first irradiation is derived with time $t_1-t_N$ from equation (5) above. Function F is determined such that the lag L due to the first irradiation and the first X-ray detection signals acquired by the first irradiation before shipment become equal (see equation (6) above).

This invention is not limited to the foregoing embodiments, but may be modified as follows:

(1) In each embodiment described above, a fluoroscopic apparatus as shown in FIG. 1 has been described by way of example. This invention may be applied also to a fluoroscopic apparatus mounted on a C-shaped arm, for example. This invention may be applied also to an X-ray CT apparatus. This invention is useful particularly when actual photography (rather than fluoroscopy) is carried out as by an X-ray radiographic apparatus.

(2) In each embodiment described above, the flat panel X-ray detector (FPD) 3 has been described by way of example. This invention is applicable to any X-ray detectors in wide use.

(3) In each embodiment described above, the X-ray detector for detecting X rays has been described by way of example. This invention is not limited to a particular type of radiation detector which may, for example, be a gamma-ray detector for detecting gamma rays emitted from a patient dosed with radioisotope (RI), such as in an ECT (Emission Computed Tomography) apparatus. Similarly, this invention is applicable to any imaging apparatus that detects radiation, as exemplified by the ECT apparatus noted above.

(4) In each embodiment described above, the FPD 3 is a direct conversion type detector with a radiation (X rays in the embodiments) sensitive semiconductor for converting incident radiation directly into charge signals. Instead of the radiation sensitive type, the detector may be the indirect conversion type with a light sensitive semiconductor and a scintillator, in which incident radiation is converted into light by the scintillator, and the light is converted into charge signals by the light sensitive semiconductor.

(5) In each embodiment described above, an operation is started to acquire X-ray detection signals in time of non-irradiation after lapse of the predetermined time (i.e. the waiting time $T_W$ in each embodiment) from the second X-ray irradiation in a preceding imaging event. Where the short and medium time constant components are at a negligible level, the acquisition of X-ray detection signals may be started simultaneously with a transition from the second X-ray irradiation in the preceding imaging event to the non-irradiation state. This applies also to radiation other than X rays.

(6) In each embodiment described above, the first correction data A serving as the basis for the lag correction includes data of X-ray detection signal $I_N$ acquired immediately before a start of the first X-ray irradiation in the current imaging event. It is not absolutely necessary to include the data of X-ray detection signal $I_N$. However, since the latest data is the most reliable, it is desirable, as in each embodiment, to obtain the first correction data A including the data of X-ray detection signal $I_N$, and perform the lag correction by removing lags using the first correction data A. This applies also to radiation other than X rays.

(7) Each embodiment described above employs the recursive weighted average (recursive process) as shown in the foregoing equation (4). The recursive computation is not limited to the recursive weighted average, but may be an unweighted recursive computation. Thus, function D ($I_N$, $A_{N-1}$) expressed by X-ray detection signal $I_N$ and the first correction data $A_{N-1}$ may be expressed by the first correction data $A_N$ to serve the purpose.

(8) The invention is not limited to function F of the first X-ray detection signals representing the second correction data B in each embodiment described above. When a constant is C, for example, equation (2) above may be trans-formed into the following equation (2)':

$$B=C \times I'_{FIRST} \qquad (2)'$$

In equation (2) above, function F becomes a linear function. When function F is a linear function, constant C may be determined such that the value of the first X-ray detection signal S multiplied by constant C becomes equal to lag L due to the first irradiation as in the following equation (6)':

$$C \times S=L \qquad (6)'$$

The linear function is not limitative, but the order may be two or more, such as a quadratic function. In addition, function F may be set as desired, such as a logarithmic function or trigonometric function.

(9) In each embodiment described above, the values (second correction data B) based on the first X-ray detection signals are determined by function F of the first X-ray detection signals. For example, a table storing values matched with the first X-ray detection signals, respectively, may be prepared, and by referring to the table, the values matched may be employed as the values based on the first X-ray detection signals. In this case, instead of determining function F by equation (6) above, the first irradiation shown in FIG. 10 may be carried out a plurality of times before shipment, with varied intensities of the first X-ray detection signals, to derive lag L due to the first irradiation for the intensity of each first X-ray detection signal. A table may be prepared storing the lags L matched with the respective first X-ray detection signals.

(10) In each embodiment described above, lag components due to the first radiation detection signals are regarded as included in the second radiation detection signals (second X-ray detection signals in each embodiment), and lag correction is further carried out for the second radiation detection signals by removing lags from the second radiation detection signals (second X-ray detection signals in each embodiment) using the values (second correction data B in each embodiment) based on the first radiation detection signals (first X-ray detection signals in each embodiment). It is not absolutely necessary to further carry out lag correction for the second radiation detection signals if there is sufficient space between the first irradiation and second irradiation and the lag components due to the first radiation detection signals are negligible.

(11) In determining function F of the first X-ray detection signals representing the second correction data B in each embodiment described above, function F may be determined as including the weights ($W_1$, $W_2$) used in the subtraction.

(12) In each embodiment described above, the first correction data A is subtracted from each radiation detection signal in order to carry out lag correction by applying lag data (first correction data A in each embodiment) to both the first radiation detection signals (first X-ray detection signals in each embodiment) and the second radiation detection signals (second X-ray detection signals in each embodiment). The first correction data A may be applied for division from each radiation detection signal, for example. The invention is not limited to a specific operation technique.

INDUSTRIAL UTILITY

As described above, this invention is suited to a radiographic apparatus having a flat panel X-ray detector (FPD).

The invention claimed is:

1. A radiographic apparatus for obtaining radiographic images based on radiation detection signals, comprising a radiation emitting device for emitting radiation toward an object under examination; a radiation detecting device for detecting radiation transmitted through the object; (1) a non-irradiation signal acquiring device for acquiring a plurality of radiation detection signals detected from the radiation detecting device in time of non-irradiation before irradiation of the radiation in an imaging event; (2) an irradiation signal acquiring device for acquiring the radiation detection signals detected from the radiation detecting device in time of irradiation of the radiation in the imaging event; (3) a lag correcting device operable, when irradiation is carried out twice across a non-irradiation, the earlier irradiation being regarded as a first irradiation and the later irradiation being regarded as a second irradiation, radiation detection signals acquired by said irradiation signal acquiring device during said first irradiation being regarded as first radiation detection signals, and radiation detection signals acquired by said irradiation signal acquiring device during said second irradiation being regarded as second radiation detection signals, for applying lag data based on a plurality of radiation detection signals acquired by the non-irradiation signal acquiring device in time of non-irradiation before the first irradiation to both said first radiation detection signals and said second radiation detection signals, to remove lag-behind parts included in the radiation detection signals from the radiation detection signals, thereby performing a lag correction of the lag-behind parts; and (4) a radiographic image acquiring device for acquiring radiographic images by performing subtraction using the first radiation detection signals and the second radiation detection signals for which the lag correction has been carried out by the lag correcting device.

2. A radiation detection signal processing method for performing a signal processing to obtain radiographic images based on radiation detection signals detected by irradiating an object under examination, said signal processing comprising (a) a non-irradiation signal acquiring step for acquiring a plurality of radiation detection signals in time of non-irradiation before irradiation of the radiation in an imaging event; (b) a first irradiation signal acquiring step for acquiring radiation detection signals in time of first irradiation which is a radiation irradiation time in the imaging event after said non-irradiation signal acquiring step; (c) a second irradiation signal acquiring step for acquiring radiation detection signals in time of second irradiation which is a radiation irradiation time in the imaging event following non-irradiation after said first irradiation signal acquiring step; (d) a lag correcting step for applying lag data based on the radiation detection signals acquired in said non-irradiation signal acquiring step to both first radiation detection signals which are the radiation detection signals acquired in said first irradiation signal acquiring step, and second radiation detection signals which are the radiation detection signals acquired in said second irradiation signal acquiring step, to remove lag-behind parts included in the radiation detection signals from the radiation detection signals, thereby performing a lag correction of the lag-behind parts; and (e) a radiographic image acquiring step for acquiring radiographic images by performing subtraction using the first radiation detection signals and the second radiation detection signals for which the lag correction has been carried out in the lag correcting step.

3. A radiation detection signal processing method as defined in claim 2, characterized in that a further lag correction is carried out for the second radiation detection signals to remove lags from the second radiation detection signals using values based on the first radiation detection signals, noting that the second radiation detection signals acquired in said second irradiation signal acquiring step include lag components due to the first radiation detection signals acquired in said first irradiation signal acquiring step.

4. A radiation detection signal processing method as defined in claim 3, characterized in that the values based on said first radiation detection signals and used in the lag correction for said second radiation detection signals are expressed by a function of the first radiation detection signals.

5. A radiation detection signal processing method as defined in claim 3, characterized in that the values based on said first radiation detection signals and used in the lag correction for said second radiation detection signals are values matched beforehand with the first radiation detection signals, respectively.

6. A radiation detection signal processing method as defined in claim 4, characterized in that said function is determined from information on radiation detection acquired before a series of radiation detection signals, acquiring conditions before the series of radiation detection signals, or peculiar information on a radiation detecting device that detects radiation detection.

7. A radiation detection signal processing method as defined in claim 5, characterized in that said values matched beforehand with the first radiation detection signals, respectively, are determined from information on radiation detection acquired before a series of radiation detection signals, acquiring conditions before the series of radiation detection signals, or peculiar information on a radiation detecting device that detects radiation detection.

* * * * *